US009989436B1

(12) United States Patent
Kofoed et al.

(10) Patent No.: US 9,989,436 B1
(45) Date of Patent: Jun. 5, 2018

(54) METHOD AND DEVICE FOR DETECTING THE LOCATION AND MAGNITUDE OF A LEAK IN A PIPE MEASURING ABERRANT ELECTROMAGNETIC RADIATION FROM WITHIN A PIPE

(71) Applicant: Willowstick Technologies, LLC, Draper, UT (US)

(72) Inventors: Val Kofoed, Spanish Fork, UT (US); Michael Jessop, Saratoga Springs, UT (US)

(73) Assignee: Willowstick Technologies, LLC, Draper, UT (US)

( * ) Notice: Subject to any disclaimer, the term of this patent is extended or adjusted under 35 U.S.C. 154(b) by 0 days. days.

(21) Appl. No.: 15/631,959

(22) Filed: Jun. 23, 2017

Related U.S. Application Data

(60) Provisional application No. 62/355,142, filed on Jun. 27, 2016.

(51) Int. Cl.
| | |
|---|---|
| *G08B 1/00* | (2006.01) |
| *G01M 3/40* | (2006.01) |
| *G01M 3/00* | (2006.01) |
| *F17D 5/06* | (2006.01) |
| *G01N 27/87* | (2006.01) |
| *G01N 27/02* | (2006.01) |

(52) U.S. Cl.
CPC ............... *G01M 3/40* (2013.01); *F17D 5/06* (2013.01); *G01M 3/005* (2013.01); *G01N 27/02* (2013.01); *G01N 27/87* (2013.01)

(58) Field of Classification Search
CPC ........... G01M 3/40; G01M 3/005; F17D 5/06; G01N 27/02; G01N 27/87
USPC ........... 340/870.11, 605, 604, 539.1, 539.11; 73/49.1, 40.5
See application file for complete search history.

(56) References Cited

U.S. PATENT DOCUMENTS

| | | | | |
|---|---|---|---|---|
| 5,986,756 A | * | 11/1999 | Slater | G01N 21/31 250/458.1 |
| 6,301,954 B1 | * | 10/2001 | Schuberth | G01M 3/18 324/358 |
| 6,539,777 B1 | * | 4/2003 | Ashworth | G01M 3/2823 73/40.5 R |
| 6,987,458 B1 | * | 1/2006 | Limmer | G08B 21/20 340/604 |

* cited by examiner

Primary Examiner — Daryl Pope
(74) Attorney, Agent, or Firm — ColterJennings

(57) ABSTRACT

Method and device for detecting the location and magnitude of a leak in a pipe by measuring aberrant electromagnetic radiation from within the pipe. A probe comprising three orthogonally oriented coils coupled to a control unit and an electrode are inserted into a pipeline trailing a metered wire. The coils detect an anomalous current flow when a leak is encountered, enabling the magnitude and location of the leak to be detected.

5 Claims, 6 Drawing Sheets

METHOD AND DEVICE FOR DETECTING THE LOCATION AND MAGNITUDE OF A LEAK IN A PIPE MEASURING ABERRANT ELECTROMAGNETIC RADIATION FROM WITHIN A PIPE

RELATED APPLICATION DATA

This application claims the benefit of the filing date of U.S. Provisional Patent Application Ser. No. 62/355,142 titled "Method and device for detecting the location and magnitude of a leak in a pipe measuring aberrant electromagnetic radiation from within a pipe" filed on 27 Jun. 2016, which provisional application is hereby incorporated herein by reference in its entirety.

BACKGROUND

The present disclosure relates to a leak detection system designed to help identify, locate, and calculate the volume of a leak in a confined water transport system such as pipelines, tunnels, aqueducts, levees, canals, and dikes. Confined water distribution systems typically have losses that may range from ten percent, in the case of reasonably new and well-maintained systems, to fifty-percent or more.

Water distribution systems within the United States and in both developed and developing nations throughout the world often compriseor include aging infrastructure wherein leaks continue unabated or arise with increasing frequency. With water shortages and pollution looming as major concerns in urban, suburban, and rural areas, the ability to rapidly and economically detect, quantify, and repair leaks in water delivery systems (and in other pipeline type delivery systems) is critical from both financial and environmental perspectives.

Traditional methods for detecting leaks in piping systems have been costly and inexact in their results. Generally, these involve direct examination of water transport systems either through excavation or by inserting a sensory probe into the transport system to visually inspect it. In many cases, small cracks or fissures that are not readily detectable even under video or tactile inspections may actually be the source of a large leak. Similarly, locating what may appear to be the source of leak can be found not to be a leak at all after the expensive and disruptive process of excavating at the location of the inaccurately determined source of a leak.

Most water transport systems are maintained by municipal governments that have fiduciary responsibility for taxpayer funds. In today's municipal infrastructure environment, such funds are limited and government bodies and regulated utility providers can ill afford a trial-and-error approach. The present disclosure below relates to a method for economical and accurate detection, quantification, and remediation support for leaks in piping systems using a probe equipped with electromagnetic sensors.

SUMMARY

The present disclosure relates to a method that detects pipe leaks by running electric current through water inside a confined water transport system and detecting where the electromagnetism produced by that electric current changes direction. This aberration in the electromagnetism is detected by the present method, using components to triangulate the location of the aberrant signal and, thereby, the location of the leak.

The method typically uses the following components:
(1) a potted coil within a gimbal oriented along x-axis;
(2) a potted coil within a gimbal oriented along y-axis;
(3) a potted coil within a gimbal oriented along z-axis;
(4) a control center (typically including a clock, battery, computer, tracking beacon, and data storage);
(5) a non-conductive, flexible conduit (may bend, but does not significantly contract or extend);
(6) a circuit wire connector and electrode;
(7) a non-conductive, flexible pull and push conduit;
(8) circuit wire;
(9) a flexible skin or housing;
(10) a tail made of conductive material;
(11) a neutrally buoyant ball (Pipeline Inspection Gauge or "PIG") or a remote operated vehicle (ROV);
(12) a pipeline (or other water conduit);
(13) a port of entry into the pipeline, including a flange with a hole sufficient to run Component 8 (circuit wire) through it once closed and a valve to release air in the pipe;
(14) a power supply;
(15) a circuit fault interrupter;
(16) a generator;
(17) a grounding electrode (to complete a circuit);
(18) a clock (synchronized with the clock in Component 4, the control center) attached to a meter that measures the length of circuit wire let out into the pipeline;
(19) a Teflon (or similar material) tube;
(20) a sanitizing tank; and
(21) a tension-controlled spool for the circuit wire.

Components 1-11 make up what can be called the "Probe." The Probe is inserted into a confined water transport system through a port of entry or other insertion mechanism. The Probe can then be moved through the system using the natural flow of water or fluid within the system for propulsion.

The coils are highly sensitive to electromagnetism. This sensitivity is most pronounced at the ends of the coils (i.e., to current running parallel with the length of the coil). Thus, by using three coils oriented orthogonally to one another (i.e., along x-, y-, and z-axes, respectively) and spaced sufficiently to avoid distortion and noise created by one another, the coils are able to detect small changes in the orientation of electromagnetism.

Where electrical current is able to escape the pipe, this is evidence of a likely fluid leak in the pipe. The electromagnetism data detected by each of the three coils are stored by the on-board computer. These data are then combined with data about the length of circuit wire extended into the pipeline to mathematically determine the location of the water leak using standard equations. This method detects not only the station of the pipe where the leak is located, but also the orientation of the leak (i.e., top, bottom, right side, left side of the pipe) and its magnitude. The readings from the coils are stored digitally in the on-board computer on local or removable data storage (e.g., flash drive, SD card, etc.).

BRIEF DESCRIPTION OF THE DRAWINGS

Illustrative embodiments are described in detail below with reference to the attached drawing figures, which are incorporated by reference herein and wherein.

DETAILED DESCRIPTION

Figure 1:
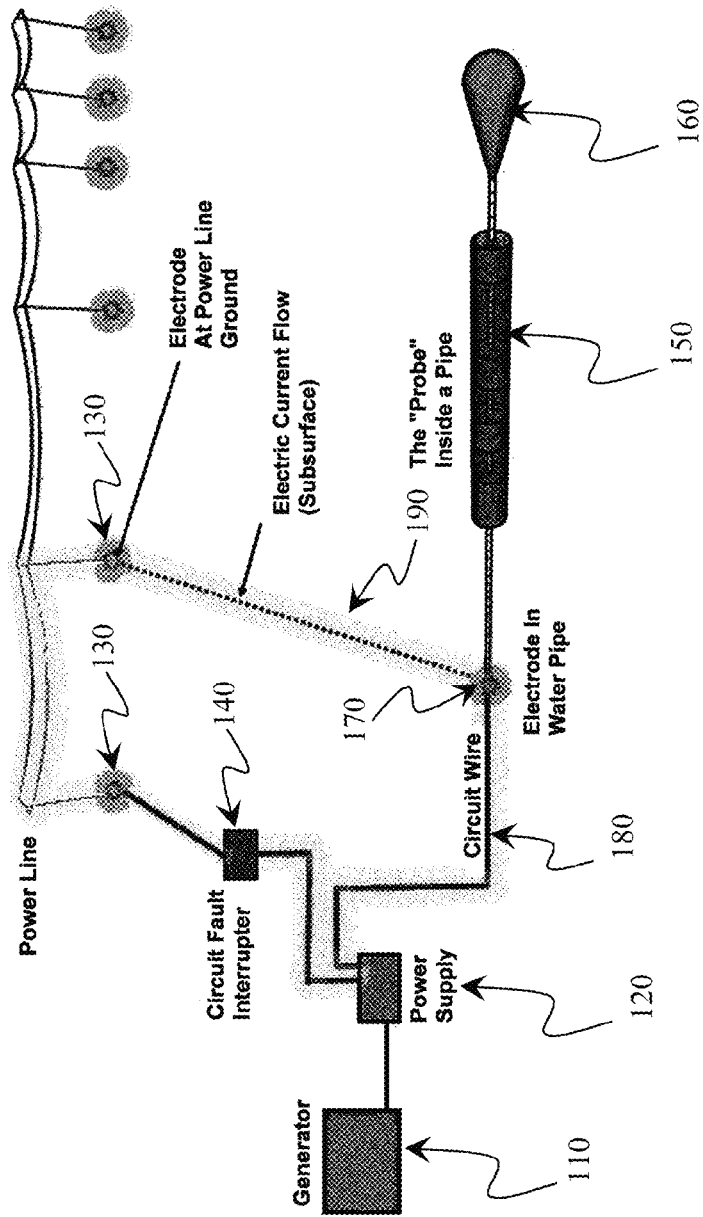
FIG. 1 depicts an overview of the device and method.

FIG. 1 provides a schematic view of the present apparatus and its working method. The apparatus locates leaks in a piping system by detecting anomalous electric current flow caused by the leak. A generator 110 provides power to a regulated power supply 120. The apparatus may use an existing power line ground 130 in which case a circuit fault interrupter 140 is used to ensure safety and isolation. This element is not required if an independent ground system not connected to an external power system is used.

A Probe 150 comprising three optionally disposed coils and a control circuit is inserted into the pipeline to be tested. The Probe is pulled through the pipe by a PIG 160, configured to fit the pipe being tested and to be propelled by the natural flow of fluid within the pipe. An electrode 170 trails after the Probe, followed by a circuit wire 180 of sufficient length to enable communication with the Probe over the desired length of pipe. The coils with the Probe detect and measure current flow 190 between the trailing electrode and the electric ground. When the Probe encounters a leak in the pipe, such leak creates an anomalous current flow that can be detected by the Probe and associated with the Probe's location within the piping system.

Figure 2:
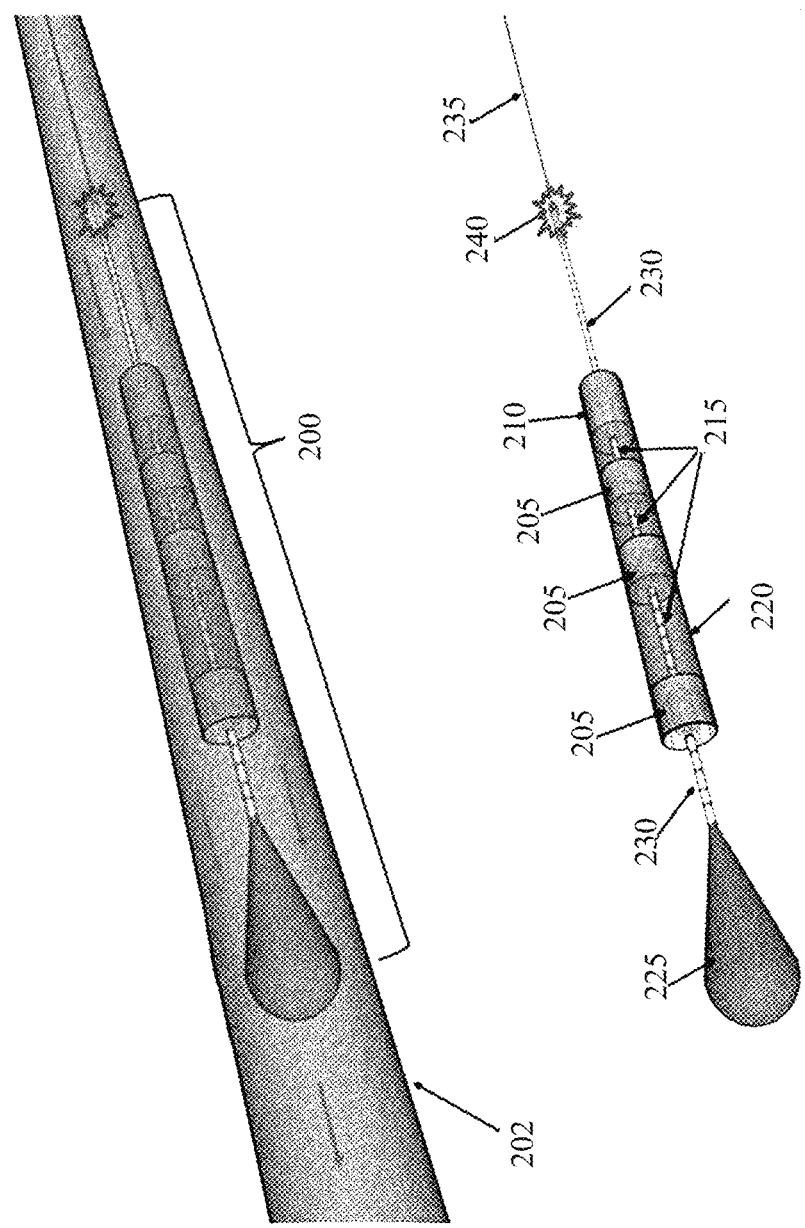
FIG. 2 depicts the various components of the Probe.

FIG. 2 shows the elements of the Probe system 200 that is inserted into a pipeline 202 to detect the presence of leaks. The three potted coils 205 are stabilized along three orthogonal axes by gimbals and the control unit 210 are individually insulated and protected by epoxy or similar material and are connected by wires inside non-conductive, flexible pull conduit 215, all of which are enclosed within a cylindrical, flexible skin or housing 220. This flexible skin and everything inside of it make up the Probe. The flexible conduit extends out of the front and back ends of the Probe 230. The PIG or ROV component 225 is attached to the front of the flexible conduit. Attached to the end of the flexible conduit protruding from the back of the Probe is a circuit wire 235 connector and electrode 240, which connects to the circuit wire. The circuit wire extends back toward a port of entry into the pipeline, through a Teflon tube to avoid abrasion on the circuit wire as it rounds the corner toward the port of entry, and beyond where it connects to a clock attached to a meter that measures the length of the circuit wire let into the pipeline, a tension-controlled spool and to a power supply 120 connected to a generator 110.

Optionally, the circuit wire may be connected to a circuit fault interrupter 140 when using existing power lines as the grounding device to complete the electrical circuit. When the existing power grid is not used as the ground, then electrodes and a long wire (running away from the pipeline area to avoid interference) are placed manually to complete the circuit.

Figure 3:
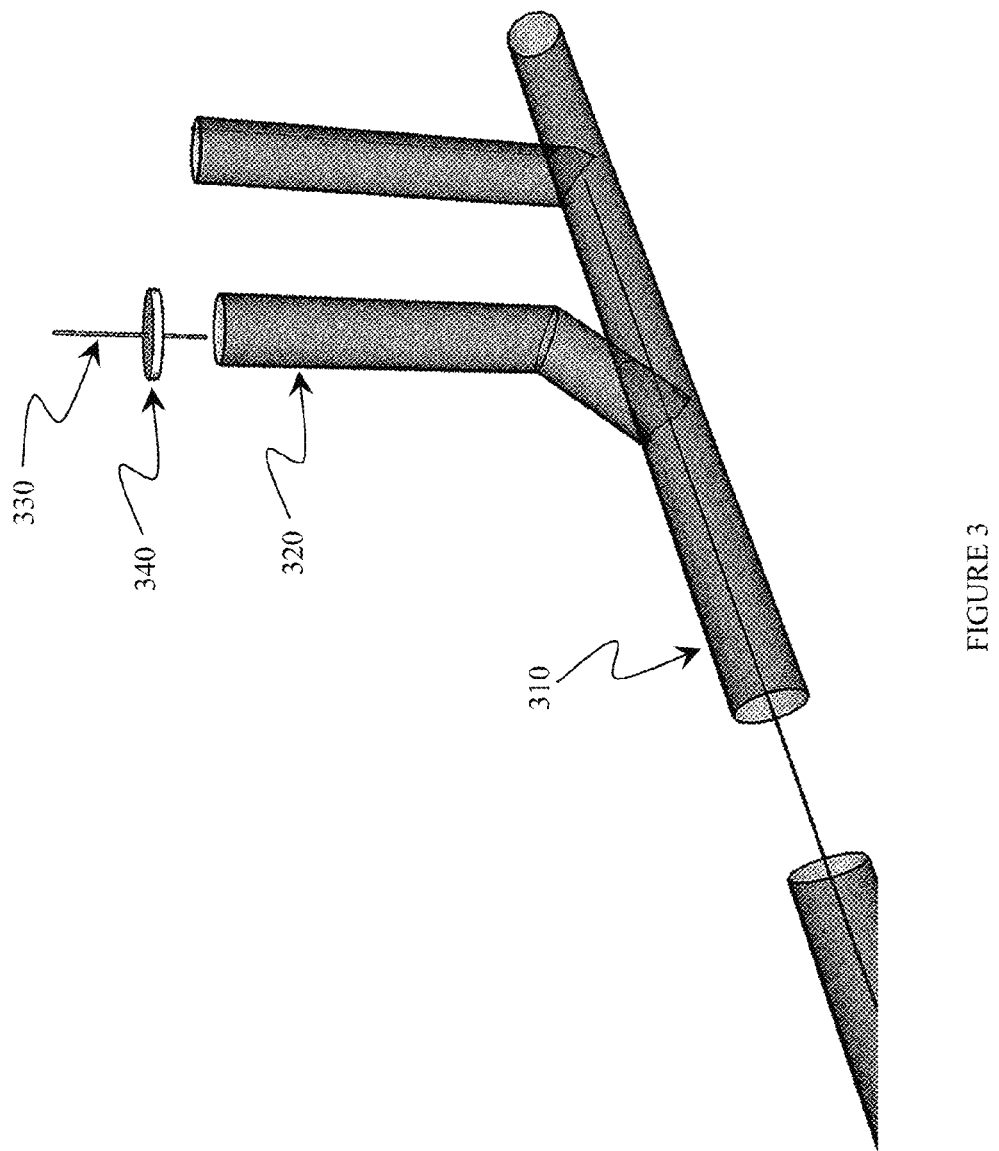
FIG. 3 depicts a port of entry into a piping system with a flange.

The Probe 230 and the PIG 225 are calibrated to be neutrally buoyant within the pipeline 202 being examined. The proper size of PIG (or ROV) is selected to fit the pipeline being examined. After turning off water flow upstream and downstream, the Probe is partially inserted into a pipeline as shown in FIG. 3. The pipe 310 to be examined is accessed through a port of entry 320. Before inserting the Probe entirely into the pipeline, the circuit wire 330 is run through a small opening in the entry port's flange 340 and connected to the electrode on the Probe 240.

Once the Probe 230 is in the pipeline 202 and connected to the circuit wire 330, the entry port flange 340 is bolted shut such that only the circuit wire is free to move in and out of the entry port, and water flow is then resumed. The Probe may be pushed or pulled through the pipeline by water flow or by manual or mechanical means (e.g., a remote operated vehicle, reeling in the circuit wire, etc.). The flange may include a valve that can be used to release pressure in the pipes.

Figure 4:
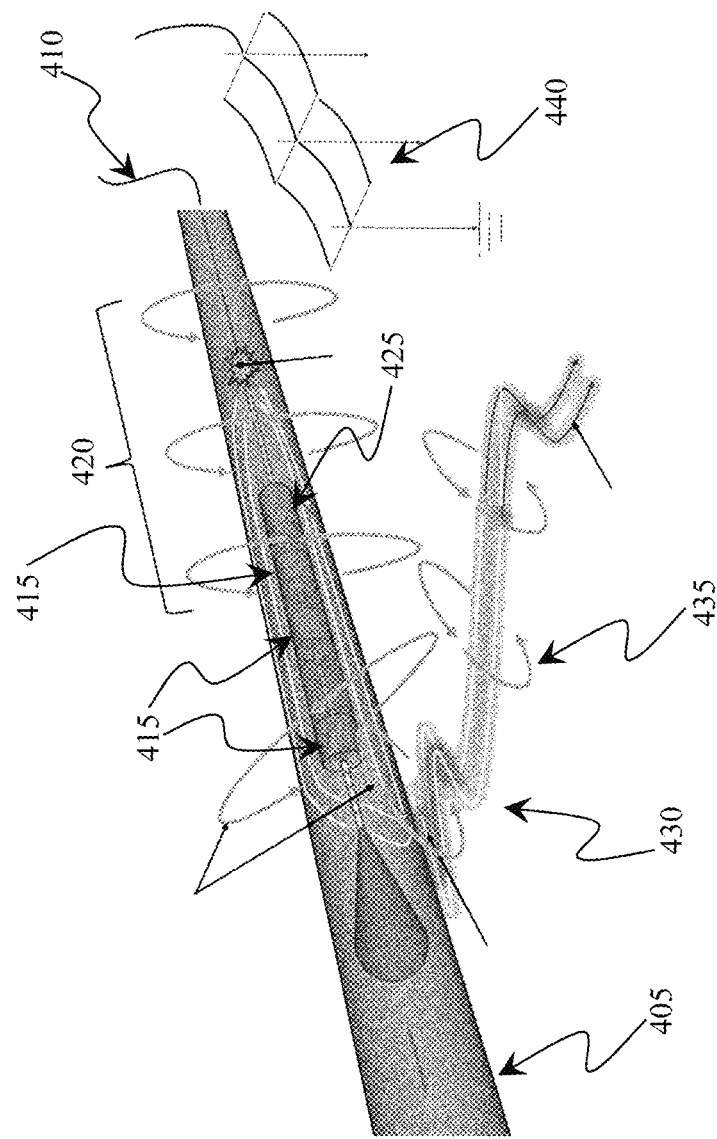
FIG. 4 depicts the Probe in operation as it encounters a leak in a confined water transport system.

FIG. 4 depicts the Probe in operation as it encounters a leak in a pipe being examined. As the Probe moves through the pipeline 405, the length of the circuit wire 410 pulled behind the probe is measured by a meter. The generator 110 and regulated power supply 120 produce an electric current of constant voltage. The potted coils 415 detect small changes in the direction and magnitude of the electromagnetism 420 produced by the charge. This information is recorded several times per second at predetermined intervals within the control center 425. The control center 425 will only record a reading if the conductive tail is in contact with the pipeline.

Gimbals keep the orientation of the coils 415 stable. Thus, the Probe 230 may twist around within the pipe without affecting the readings. Typically, the gimbal arrangement allows rotation on only two axes so that the primary axis of each coil remains in alignment with the pipe through which it is passing—one coil maintaining a longitudinal orientation, one perpendicular to the pipe horizontally, and the third perpendicular to the pipe vertically. The gimbal may maintain orientation by means of a weighted, gravity-driving system, or could be controlled by a multi-axis sensor and powered rotational mechanisms.

The coils 415 used in the Probe 230 are very sensitive to minor changes in electromagnetic fields (within one picotesla). Furthermore, the present method may be tuned or calibrated to detect electromagnetism within a specified frequency range. By adjusting the frequency of the electric current that is generated, and by calibrating the control center 425 to only record measurements of electromagnetism within that certain frequency, the present method is able to isolate the electrical current in the water from other detectable electromagnetic fields. In one embodiment an electric source of 380 Hz alternating current is used. The frequency may be varied to produce optimum sensitivity for a given environment and to avoid confusion with extraneous harmonics resulting from 50 Hz or 60 Hz line current or other nearby sources.

Water that is able to escape the pipeline 430 (e.g. a water leak) carries the electrical current 435 with it. Once outside of the pipeline, the electrical current attempts to complete a circuit. That circuit is most likely to be completed via the grounded electrode 440, which may be placed manually by the user or may be an existing electrode connected to the local power grid (when the present method is used in connection with a circuit fault interrupter connected to the power line).

When the electrical current leaves the pipeline 405, the coils 415 detect the resulting change in the magnetic field, which detection is recorded by the control center 425. The three-axis orientation of the three coils, in combination with the location of the Probe 425, as determined by the meter, are capable of recording data sufficient to calculate the location and magnitude of the electrical current escaping the pipeline and, thereby, the location and magnitude of the leak in the pipeline. The present method can record readings both while the Probe moves away from the entry port and while the Probe is reeled back in.

Figure 5:
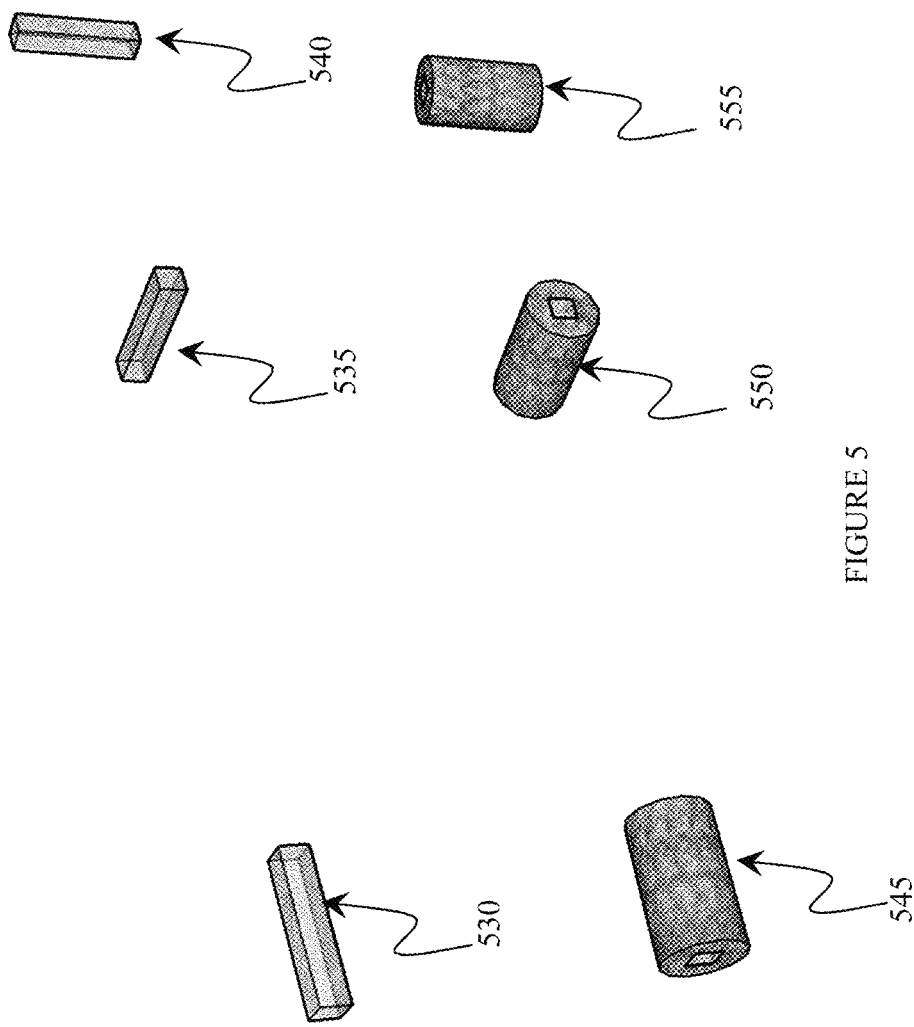
FIG. 5 depicts the orthogonal coil cores and windings.

FIG. 5 depicts the cores, windings, and relative spacing comprising the three orthogonal coils. The cores of ferrous materials are configured along three orthogonal axes, denoted X 530, Y 535, and Z 540. The windings around the cores align with the cores on the same X 545, Y 550, and Z 555 axes. Typically the X axis, which is longitudinal along the direction of the pipe, is spaced further than the distance between the Y and Z axis coils to minimize interference with those coils.

Figure 6:
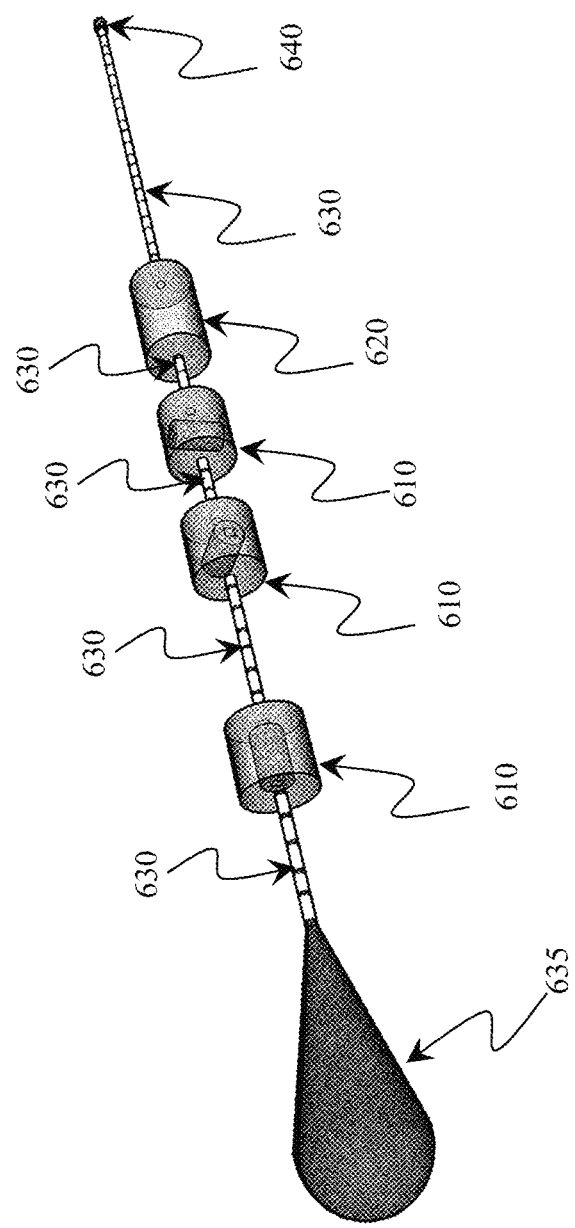
FIG. 6 depicts the encapsulated coils and control center, connecting conduit, PIG, and electrode comprising the complete Probe.

FIG. 6 shows the orientation and relative spacing of the three coils 415 within their waterproof containers 610 and the control center 620 that trails behind the coils. The control center 620 can be included as part the WILD™ (Willowstick Inline Leak Detection) configuration or it can be external to the confined water flow system (pipelines, canal, water tunnel, aqueduct, levee, dike, etc.). FIG. 6 depicts an example of an inline control center. Flexible push-pull conduit 630 connects the PIG 635, the coil units, the control unit, and leads to the trailing electrode 640 and circuit wire 235. As noted, the leading coil along the longitudinal axis of the pipeline is spaced further from the other two coils to avoid interference.

The present method is suitable for use in pipes made of a variety of materials. Even in iron or other conductive pipes, the present method is effective because the interference created by the conductive pipes is fairly consistent and can be controlled for and nulled out in the analysis of the readings.

The present method may also, but need not, accommodate a sanitizing tank through which the components that pass through the entry port are sanitized prior to entry. This sanitizing process is necessary in certain jurisdictions where the Probe 230 and other components will be in contact with culinary water and must meet certain standards, including NSF certifications and regulations. For example, the trailing cable can pass through a chlorinated bath of the appropriate concentration as it passes into the access port 320 to ensure that sanitation is maintained and that there is no adverse impact on the existing chlorination levels. The sanitation bath may be integrated with the flange 340 mounted at the port of entry coupled to the pipeline 310. Additionally, the main components may be stored in chlorinated water (or other sanitizing solutions) without damage.

If the circuit wire breaks, the Probe 230 can be located via a tracking beacon that emits a trackable wireless signal at predetermined time intervals while the control center 210 is powered on or, in a separate embodiment, the beacon could be activated via the control center if a break, decoupling, or other anomaly in the trailing cable is detected.

The disclosure above provides several advantages over prior methods. Although the foregoing description contains many specifics, these are not to be construed as limiting the scope of the present disclosure, but merely as providing certain embodiments. Similarly, other embodiments of the invention may be devised that do not depart from the scope of the present disclosure. For example, features described herein with reference to one embodiment also may be provided in others of the embodiments described herein. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

The invention claimed is:

1. An apparatus for detecting leaks in a confined fluid transport system, the apparatus configured to be inserted into a port of entry into the confined fluid transport system, the apparatus comprising:
a monitoring probe comprising:
a first gimbal containing a potted coil that is oriented along a first x-axis;
a second gimbal containing a potted coil that is oriented along a second axis that is perpendicular to the first axis;
a third gimbal containing a potted coil that is oriented along a third axis that is perpendicular to the first axis and to the second axis;
a control center comprising a first clock, a battery, a computer processing unit, a tracking beacon, and data storage;
a water-resistant housing that holds the gimbals and the control center
a non-conductive, flexible push-pull conduit connecting the three gimbals and the control center at predetermined distances from each other;
an electrode in electrical communication with the control center and that is attached to a circuit wire that is configured to trail behind the housing when the apparatus is in motion within the confined fluid transport system; and
at least one of a neutrally buoyant ball or a remote operated vehicle (ROV) to move the through the confined fluid transport system;
a regulated power supply for providing constant known voltage;
a circuit fault interrupter;
a generator to produce power to the regulated power supply;
a grounding electrode in electrical communication with the control center; and
a second clock synchronized with the first clock and electrically connected to a meter that measures the length of the circuit wire trailing the control center when moving through the confined fluid transport system.

2. The apparatus of claim 1 wherein the port of entry comprises a tube having a low coefficient of friction and configured to allow the circuit wire to pass through the port of entry without damage.

3. The apparatus of claim 1 further comprising a sanitizing tank.

4. The apparatus of claim 1 further comprising a tension-controlled spool for the circuit wire.

5. A method of detection and location of leaks in a confined fluid transport system having a known physical configuration comprising the steps of:
inserting in to the confined fluid transport system a monitoring probe, the probe comprising:
a first gimbal containing a potted coil that is oriented along a first x-axis;
a second gimbal containing a potted coil that is oriented along a second axis that is perpendicular to the first axis;
a third gimbal containing a potted coil that is oriented along a third axis that is perpendicular to the first axis and to the second axis;
a control center comprising a first clock, a battery, a computer processing unit, a tracking beacon, and data storage;
a water-resistant housing that holds the gimbals and the control center a non-conductive, flexible push-pull conduit connecting the three gimbals and the control center at predetermined distances from each other;

an electrode in electrical communication with the control center and that is attached to a circuit wire that is configured to trail behind the housing when the apparatus is in motion within the confined fluid transport system; and at least one of a neutrally buoyant ball or a remote operated vehicle (ROV) to move the probe through the confined fluid transport system;

using a regulated power supply to provide a constant known voltage to the probe, the power supply being powered by a generator;

incorporating a grounding electrode in electrical communication with the control center to close a circuit that includes the probe;

stopping the flow of fluid through the confined fluid transport system;

introducing the probe into the confined fluid transport system, optionally passing the probe through a sanitizer when desirable or required;

starting the flow of fluid through the confined fluid transport system at a predetermined rate of flow;

moving the probe through at least a portion of the confined fluid transport system while trailing a length of the circuit wire behind the moving probe;

continuously measuring the length of circuit wire that enters the confined fluid transport system to determine the location of the probe within the confined fluid transport system;

continuously monitoring electromagnetic fields sensed by the potted coils within the probe;

identifying anomalies in the electromagnetic fields to detect leaks in the confined fluid transport system; and determining the location of a leak by comparing when an anomaly is identified and the length of the circuit wire that has entered the confined fluid transport system and mapping that length to the physical configuration of the confined fluid transport system.

* * * * *